United States Patent [19]
Dillard, III et al.

[11] Patent Number: 5,279,584
[45] Date of Patent: Jan. 18, 1994

[54] ROTARY LOCK FOR NEEDLE SHEATHS

[75] Inventors: John A. B. Dillard, III, Camarillo; James A. Orr, Goleta, both of Calif.

[73] Assignee: Square One Medical, LP, Camarillo, Calif.

[21] Appl. No.: 55,801

[22] Filed: Apr. 30, 1993

Related U.S. Application Data

[63] Continuation of Ser. No. 803,578, Dec. 9, 1991, abandoned.

[51] Int. Cl.⁵ .............................................. A61M 5/32
[52] U.S. Cl. .................................. 604/198; 604/263
[58] Field of Search ............... 604/110, 187, 192, 198, 604/263

[56] References Cited

U.S. PATENT DOCUMENTS 5,088,988 2/1992 Talonn et al. ..................... 604/198
5,104,385 4/1992 Huband .............................. 604/198

*Primary Examiner*—John D. Yasko
*Attorney, Agent, or Firm*—Ladas & Parry

[57] ABSTRACT

This specification discloses a lock for a latch on a hypodermic syringe which has a reciprocating sheath that is normally latched to cover the needle to protect persons handling the syringe. The latch is operated to withdraw the sheath to expose the needle for use. The latch shell 22 is moved longitudinally to actuate latch fingers 26. After use it is desirable to lock the latch to prevent reuse of the syringe. A user manually rotates the latch shell 20 to lock the latch in the position where the sheath is over the needle. Rotary motion causes the lugs 26 to ride up the ramps 28 and then drop into the recesses 29. Thereafter, there can be no rotation and no reciprocation of the latch. The lugs prevent rotary motion as well as reciprocating motion of the latch shell 22.

18 Claims, 4 Drawing Sheets

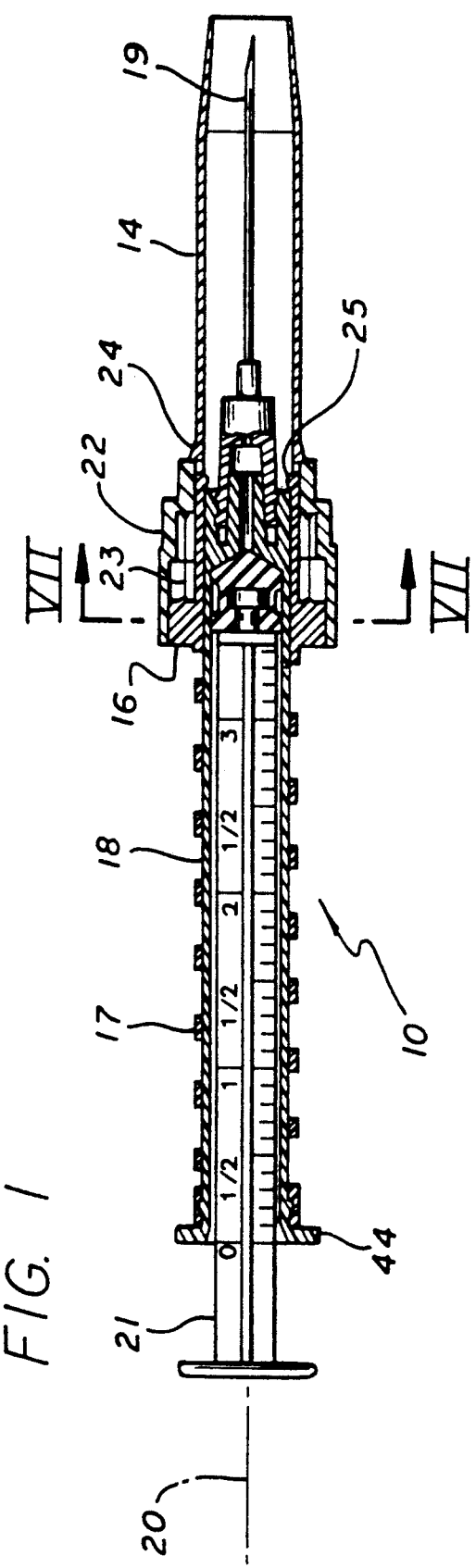
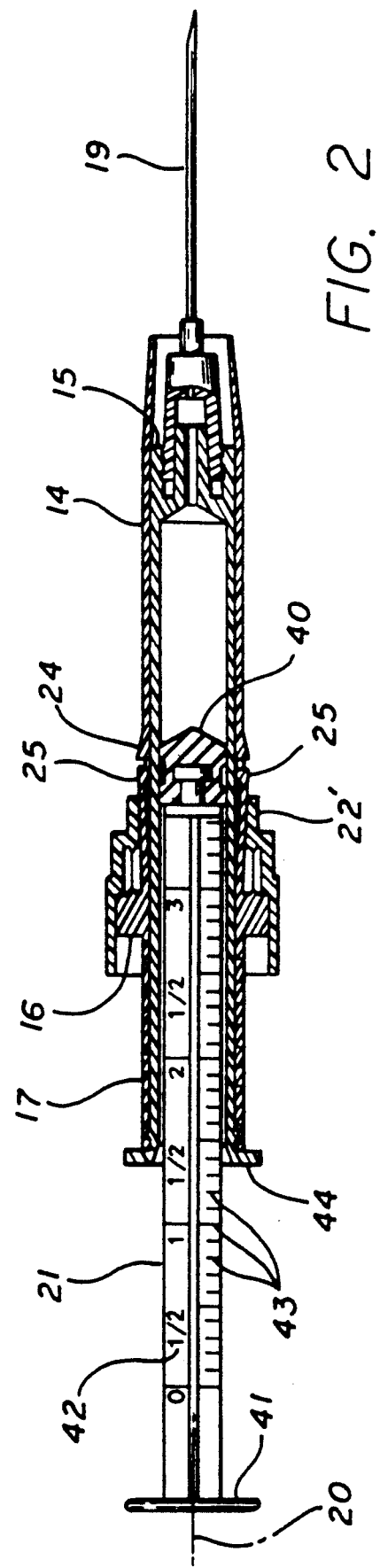

ROTARY LOCK FOR NEEDLE SHEATHS

This is a continuation of co-pending application Ser. No. 07/803,578 filed Dec. 9, 1991, now abandoned.

This invention relates to hypodermic syringes of the type that has a movable sheath over the needle and in particular to a rotary lock which permanently holds the sheath in its protective position over the needle.

BACKGROUND OF THE INVENTION

The advent of the AIDS virus requires that structures of the greatest safety be employed for hypodermic needle syringes. While blood extraction for diagnosis is an important area of hypodermic needle contamination, a much more frequent use of hypodermic needles occurs in the injection of medicine, anesthesia, and various liquids. Once an injection is made and the needle withdrawn from the patient, the needle tip is contaminated with the microorganisms of the patient. Thereafter, any accidental pricking of another person by the needle will transfer to that person such microorganisms. Various sliding sheaths have been devised that remain mechanically connected to the syringe at all times. Usually, these sheaths are spring-biased to cover the needle. However, if the sheath contacts a person it will retreat and slide until the needle penetrates that person, passing on the contamination. The contamination is injected under the skin, an area where it cannot be easily removed and where the contamination is most likely to spread. For this reason, latches of various types have been used to hold the sheath in its protective position over the needle.

BRIEF DESCRIPTION OF THE INVENTION

The present invention provides a lock for protective sheaths, and the lock permanently holds the sheath over the needle when the operator is finished using it. The lock may be applied to the sheath-latching mechanism to hold the latch in the position wherein the sheath is covering the needle. The lock includes a ramp in a plane transverse to the sliding motion of the sheath, and it further includes a lug that rides up the ramp to drop into a recess at the end of the ramp. In this fashion, manual rotation of the latch causes the latch to be permanently held in the sheath-extended position and to thereby protect persons coming in contact with syringes.

DESCRIPTION OF THE DRAWINGS

The drawings form an integral part of the specification, and:

FIG. 1 is a sectional elevation view through a hypodermic syringe wherein a latch holds the sheath in an extended position covering the needle.

FIG. 2 is a sectional view through the structure of FIG. 1 wherein the latch has been manually operated to release the sheath and the sheath has been manually withdrawn so that the needle may be used.

DETAILED DESCRIPTION OF THE DRAWINGS

Figure 3:
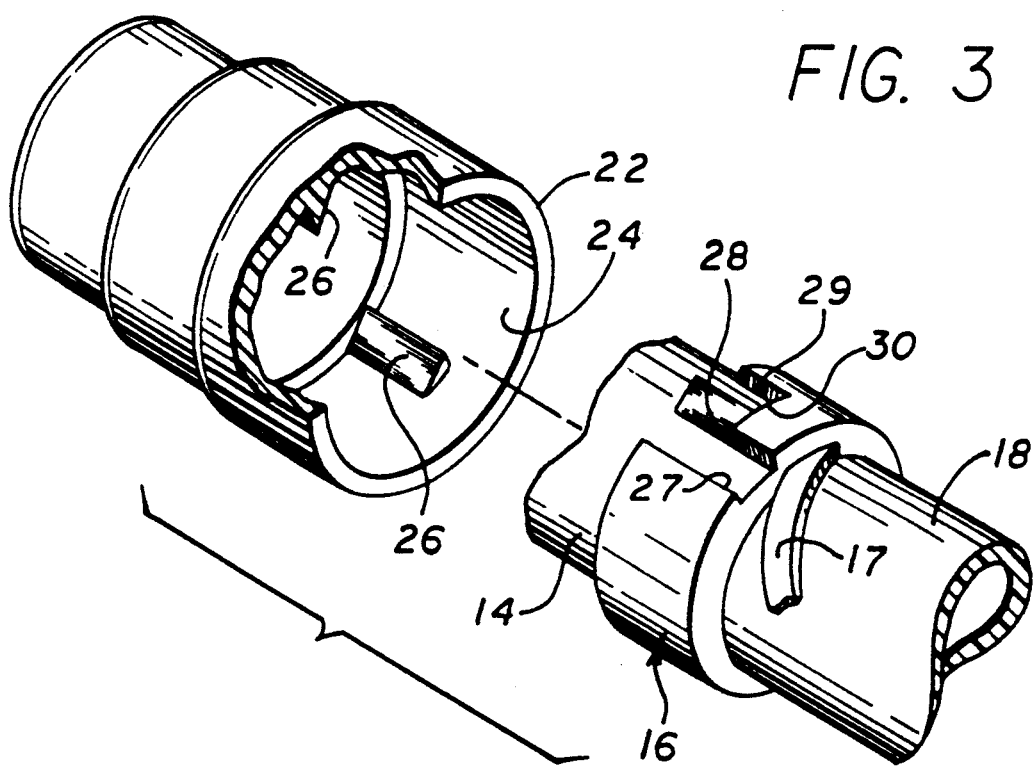
FIG. 3 is a three-dimensional exploded view on an enlarged scale looking toward the needle of the latch of FIGS. 1 and 2 showing one of two ramps that terminates in a recess so that relative rotation between the two parts results in locking a lug into the recess.
Figure 4:
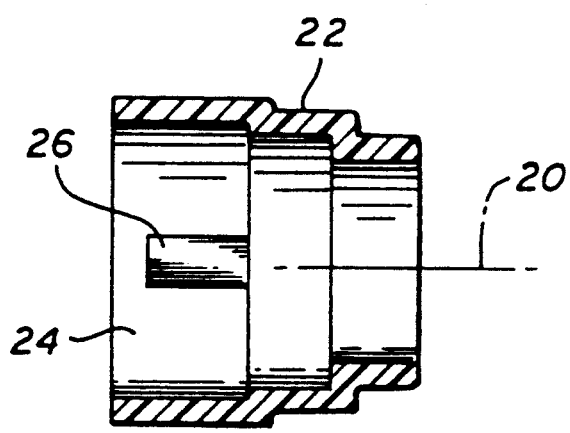
FIG. 4 is a sectional view through the outer sliding part of the latch of FIGS. 1 through 3.
Figure 5:
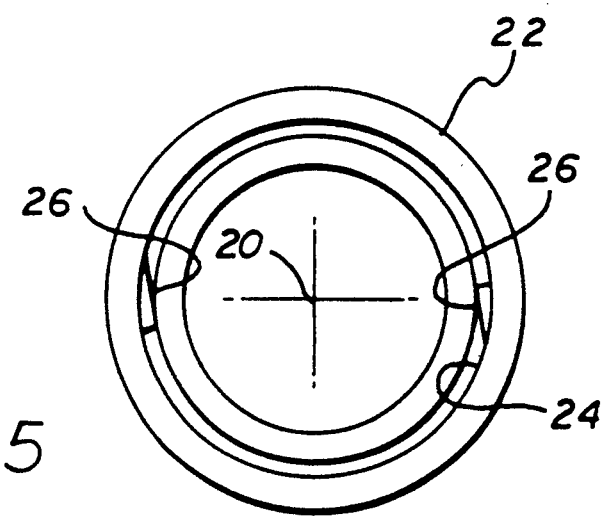
FIG. 5 is an end view of the outer latch part of FIG. 4.

Referring to FIGS. 1 and 2, a presently preferred form of hypodermic syringe 10 has a reciprocable sheath 14, a latch base 16, and an expansion spring 17. These three parts may be formed of a single piece of material, such as an injection plastic molding. The sheath 14 reciprocates on a hollow syringe body 18 having a hollow needle 19 connected to one end and a manually operated plunger 21 on the other. When there is liquid in the syringe body 18, manually pressing the plunger to the right results in ejecting the liquid through the hollow needle 19.

The syringe has a longitudinal axis 20 through the body 18 and needle 19. The latch mechanism has a reciprocating outer shell 22 which is urged to the right by an expansion spring 23, one end of which bears against the annular latch base 16. The movement to the right of the outer shell 22 is halted by tabs 24 cut from the sheath 14 and bent radially outwardly.

The latching action is accomplished by a pair of latch fingers 25 that normally spring radially outwardly as shown in FIG. 2, but are forced radially inwardly by the right end of the outer latch shell 22 when it is moved to the right as shown in FIG. 1. These fingers 25 are integrally connected to the sheath 14. When they are forced inwardly as shown in FIG. 1, they contact the right end of the hollow syringe body, and this prevents the sheath 14 from moving to the left. The latch spring 23 normally urges the outer latch shell 22 to the right, which holds the sheath in its extended position as shown in FIG. 1.

When the operator is finished with the syringe, the spring 17 will cause the sheath 14 to cover the needle 19 as shown in FIG. 1. The latch spring 23 will move the latch shell 22 to the right, forcing the fingers 25 inwardly to hold the sheath in its extended or covering position. No amount of blows on the sheath will cause it to reciprocate. Therefore, if the syringe contacts other persons, they are completely safe from the needle 19.

However, to prevent a person from operating the latch 16-22-23, and thereby reusing the now contaminated syringe, it is desirable to lock the latch and the sheath so that the sheath 14 remains permanently extended over the needle 19.

This structure locking the latch is illustrated in FIG. 3, wherein the latch of FIGS. 1 and 2 is viewed looking toward the needle 19. The outer shell 22 has a cylindrical bore 24 in which is formed a pair of lugs 26 in the shape of elongated ramps having generally parallel inclined surfaces.

The latch base 16 of FIG. 3 has a pair of longitudinal slots 27 (only one shown in FIG. 3) in which normally slide the lugs 26 of outer shell 22 as the outer shell is manually reciprocated to latch and unlatch the sheath 14. Adjoining one edge of the slots 27 is a ramp 28 having an incline in a plane transverse or perpendicular to the axis 20 (FIGS. 1 and 2). A similar slot 27 and ramp 28 are disposed on the bottom part of latch base 16 of FIG. 3. The upper ends of these ramps 28 end in recesses 29 which lock in any member that climbs up the ramp. Therefore, when the outer shell 22 is telescoped over the base 16, but is pulled forward against tabs 24 (FIG. 1), the right hand end of lugs 26 will clear slot 27, and clockwise rotation of the outer latch shell 22 will cause lugs 26 to ride up ramps 28 until they clear the ramps 28, whereupon the lugs 26 drop into the recesses 29. These recesses 29 hold the lugs 26 and prevent any rotation of shell 22 in either direction. More importantly, the right hand end of lugs 26 butt against the back end 30 of recess 29, preventing any reciprocations of shell 22. The sheath 14 is thereby permanently locked in its position over the needle 19 as shown in FIG. 1.

Figure 6:
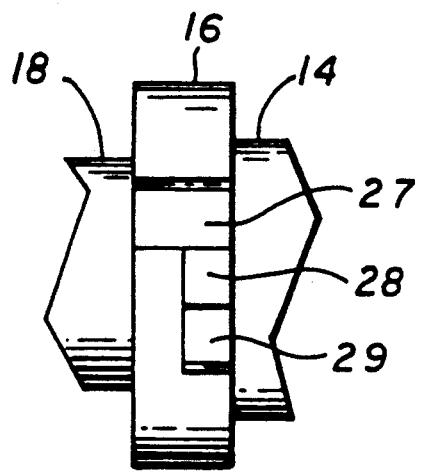
FIG. 6 is an elevation view of the inner latch part of FIGS. 1 and 2.
Figure 7:
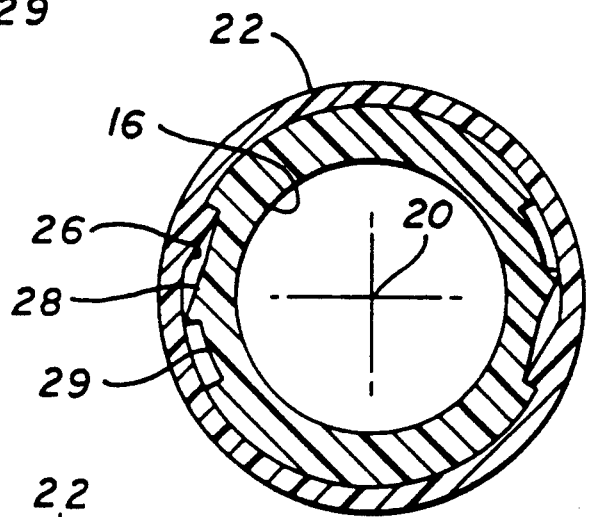
FIG. 7 is a cross-sectional view along the line VII—VII of FIG. 1 showing lugs and ramps in their normal position allowing manual sliding operation of the latch to extend or retract the sheath.
Figure 8:
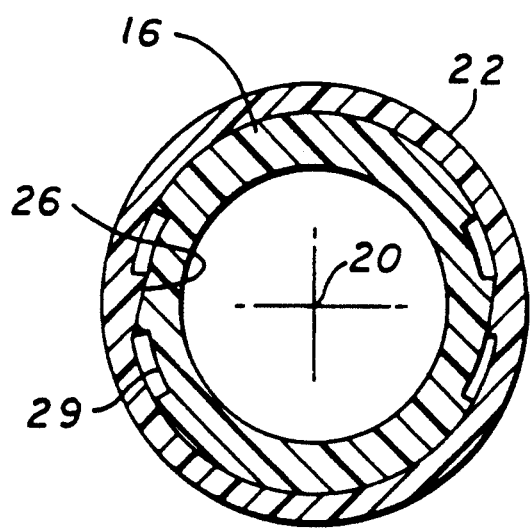
FIG. 8 is a sectional view showing the lugs and ramps rotated partway through the locking rotation.
Figure 9:
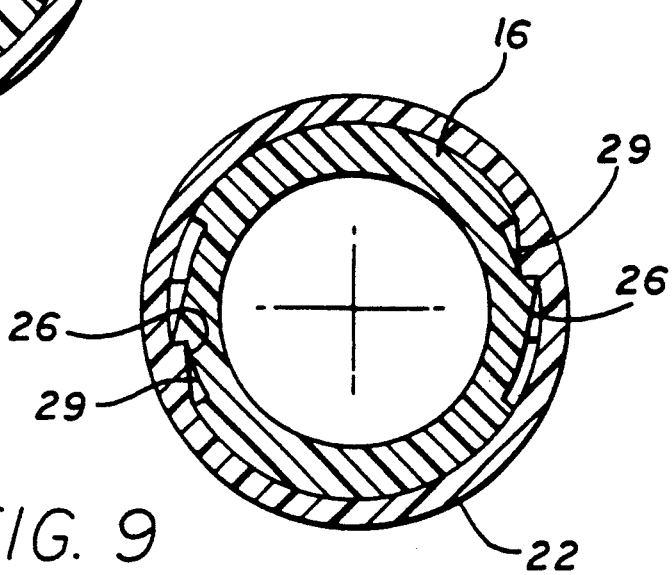
FIG. 9 is a sectional view showing the ramps fully rotated wherein lugs are disposed in the recess of the other ramps.

Shown in FIG. 6 is an elevation view of the latch base 16 and its integral sheath 14, as well as the syringe body 17 over which it reciprocates. Shown in FIG. 7 are the outer shell 22 and base 16 in the normal rotary position, permitting sheath retraction as in FIG. 2. Shown in FIG. 8 is the relation of parts about halfway through the locking rotation. Shown in FIG. 9 is the fully locked position of parts, wherein lugs 26 are seated in the recesses 29 and further rotation in either direction is not possible.

Figure 12:
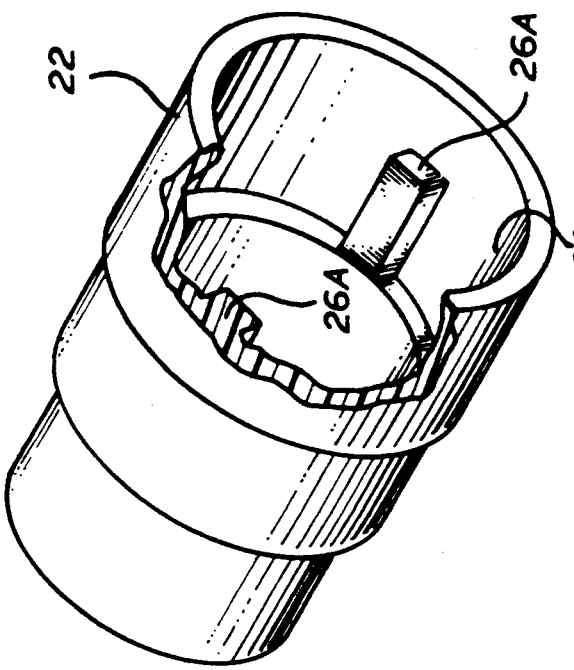
FIG. 12 is a modified form of the latch of FIG. 3 wherein flat-topped lugs are used instead of inclined lugs.

It will be appreciated that elastic deformation of the latch shell 22 and possibly the latch base 16 occurs when the lugs 26 ride up the ramps 28. This is accommodated by making these parts of elastically deformable plastic. It will be further appreciated that the ramp shape of lugs 26, nevertheless, causes the lugs to be held in the recesses 29. The inclined surface of lug 26 reduces the manual effort to make the lug 26 ride up the ramp 28. Shown in FIG. 12 are modified lugs 26A, which are in more usual lug shape. When they are seated in recesses 29, there is absolutely no rotation of shell 22. It will also appreciated that the lugs could be placed on the base 16 and the ramps 28 on the shell 22.

MODIFICATION

Figure 10:
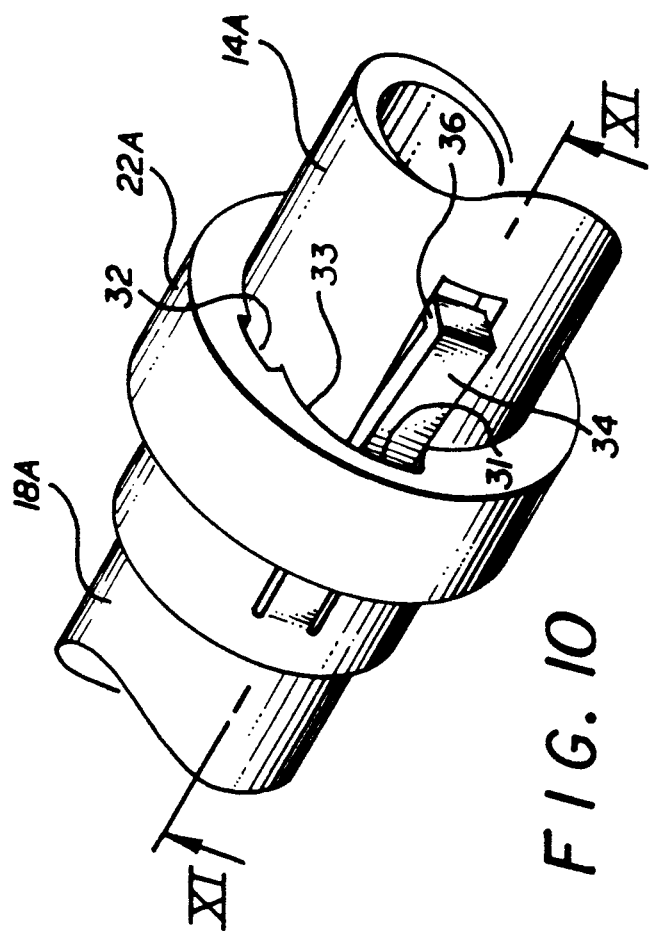
FIG. 10 is a three-dimensional view of a modified form of the invention wherein a rotary latch ring acts directly on a latch member to hold the sheath in an extended position.
Figure 11:
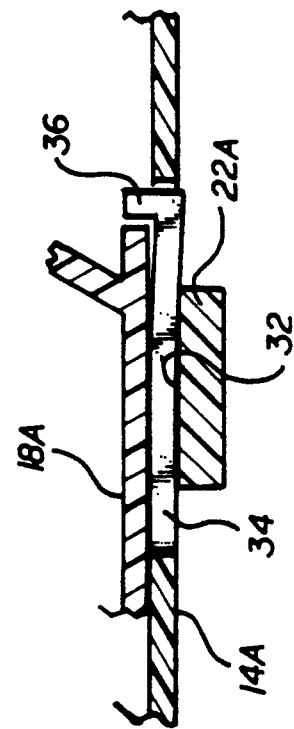
FIG. 11 is a partial sectional view along the line XI—XI of FIG. 10.

Shown in FIGS. 10 and 11 is a modified form wherein the rotary motion locks the sheath and syringe body directly rather than locking the latch. A sheath 14A telescopes over a syringe body 18A and carries a rotatable ring 22A, which has a normal slot 31 and a locking slot 32 having a ramp 33 joining them. A finger 34 formed from the sheath 14A has a hook 36 on its outer end. The finger has a built-in bias causing it to normally position itself radially outwardly as shown in FIG. 10. The rotary ring 22A may be manually reciprocated to the right to force the finger 34 inwardly to the sheath 14A in its extended position. When the operator has finished using the syringe, the latch ring 22A is manually rotated counterclockwise and the ramp 33 forces the finger 34 radially inwardly until it seats in locking slot 32. This locks the finger radially inwardly as shown in FIG. 11, and movement of the sheath 14A to the left is prevented by the hook 36 engaging the syringe body 18A. In effect, the body of finger 34 acts like a lug.

OPERATION

Referring to FIG. 1, the expansion spring 23 forces latch shell 22 to the right, which engages fingers 25, which in turn engage the syringe body 18, preventing the sheath 14 from moving to the left. This is the normal state of the syringe.

When it is desired to retract the sheath 14 and use the syringe, the operator manually moves the latch shell 22 to the left and fingers 25 spring outwardly as shown in FIG. 2. The sheath 14 can then be manually pulled to the left against spring 17. The needle is now usable as shown in FIG. 2.

If the syringe has now been used and it is desired to permanently lock the sheath over the needle to prevent accidental reuse, the relation of parts is shown in exploded view in FIG. 3. The latch shell 22 is normally telescoped over latch base 16, and the lugs 26 slide in the grooves 27. To lock, the shell 22 is moved to the left until it abuts tabs 24 (FIG. 1). The ends of the lugs 26 now clear groove 24, and clockwise rotation of the shell 22 relative to the latch base 16 causes lugs 26 to ride up the ramps 28 until they snap back into recesses 29. Thereafter, the latch is inoperable and the sheath 14 is permanently held over the needle 19.

A different shape of lug 26A is shown in FIG. 12. FIGS. 10 and 11 show a modified form of the rotary locking mechanism, wherein counterclockwise rotation of latch 22 causes the finger to snap into locking recess 32, preventing sheath retraction as shown in FIG. 11.

The invention has been described with reference to presently preferred embodiments of the invention as required by the statutes. Various modifications and variations will occur to the those in the art. All such modifications and variations that fall within the true spirit and scope of the invention are included within the scope of the following claims.

We claim:
1. A syringe comprising:
    a) a hollow syringe body having a longitudinal axis;
    b) a hollow needle communicating with the hollow syringe body;
    c) a sheath reciprocal along said axis to cover and uncover the needle;
    d) a latch reciprocal on an exterior of said sheath to latch the sheath in an extended position over the needle or to unlatch the sheath for retracting the sheath to expose the needle;
    e) a lug on one of said sheath and latch and projecting toward the other of said sheath and latch;
    f) a longitudinal slot on the other of said sheath and latch and in which the lug reciprocates for reciprocation of the latch; and
    g) a recess communicating with the slot and having a transverse wall; whereby rotating the latch with respect to the sheath disposes the lug in the recess and reciprocation of the latch is prevented by the lug abutting the transverse wall.
2. A syringe comprising:
    a) a hollow syringe body having a longitudinal axis;
    b) a hollow needle communicating with the hollow syringe body;
    c) a sheath reciprocal along said axis to cover and uncover the needle;

d) a latch reciprocal on an exterior of said sheath to one position to latch the sheath in an extended position over the needle and reciprocal to another position to unlatch the sheath for retracting the sheath to expose the needle; and e) means for locking the latch in said one position to thereby lock the sheath over the needle to prevent reuse of the syringe.

3. A syringe for use with a needle, said syringe comprising:
   (a) a hollow syringe body having a longitudinal axis;
   (b) a fitting on said body adapted to receive the needle, said fitting having an orifice in fluid communication with the hollow portion of said body and the needle;
   (c) a sheath reciprocal along said axis to cover and uncover the needle when received on said fitting;
   (d) a latch reciprocal relative to said sheath for latching said sheath in an extended position over said fitting for covering said needle when it is received on said fitting and for unlatching said sheath for retracting said sheath to expose the needle when received on said fitting;
   (e) a lug on one of said sheath and said latch, said lug projecting towards the other of said lug and sheath;
   (f) a longitudinal slot on the other of said sheath and latch, said lug reciprocating in said slot with reciprocation of said latch; and
   (g) a recess communicating with said slot, said recess having a transverse wall, whereby rotation of said latch with respect to said sheath disposes said lug in said recess which inhibits uncovering of the needle, when received on said fitting, by said lug abutting said transverse wall.

4. A syringe for use with a needle, said syringe comprising:
   (a) a hollow syringe body having a longitudinal axis, said hollow body communicating with the needle;
   (b) a sheath reciprocal along said axis to cover and uncover the needle;
   (c) a latch reciprocally mounted on an exterior of said sheath, said latch being moveable to one position to latch said sheath over the needle and to another position to unlatch said sheath for retracting said sheath to expose the needle; and
   (d) means for locking the latch in said one position to thereby inhibit uncovering of the needle by said sheath and reuse of said syringe.

5. The syringe of claim 4, further including a spring for urging said latch into said one position.

6. The syringe of claim 5 wherein said means for locking comprises a lug and a recess for receiving said lug, said lug and said recess being disposed in said sheath and said latch.

7. The syringe of claim 6 wherein said recess has a generally L-shaped configuration, the lug reciprocating in one leg of the L-shaped configuration with reciprocation of said sheath and the lug moving in the other leg of said L-shaped configuration when said latch is locked.

8. The syringe of claim 7 wherein said other leg of the L-shaped configuration includes over center means which provides a snap-action when said latch is locked by said locking means, the snap-action providing tactile feedback to a user of said syringe confirming that the sheath is locked in place.

9. The syringe of claim 8 wherein said other leg of the L-shaped configuration includes a first wall inhibiting reciprocation of said latch and a second wall inhibiting movement of said lug in said other leg from an end of said other leg remote from said one leg to said one leg.

10. The syringe of claim 9 wherein said over center means includes a ramped surface disposed adjacent said second wall.

11. In a syringe having:
   (a) a hollow syringe body having a longitudinal axis,
   (b) a hollow needle communicating with the hollow syringe body,
   (c) a sheath reciprocal along side axis to cover and uncover the needle, and
   (d) a latch reciprocal on said sheath to latch the sheath in its extended position over the needle or to unlatch the sheath for retracting the sheath to expose the needle, a lock for the latch comprising:
   1) a ramp in a plane transverse to the body axis and terminating in a recess and connected to one of said latch and sheath, and
   2) a lug connected to the other or said latch and sheath and disposed adjacent to the ramp when the latch is in its position latching the sheath in its extended position covering the needle, whereby relative rotation of the latch and the sheath causes the lug to climb the ramp and drop into the recess and thereby permanently lock the latch in a position covering the needle.

12. The rotary lock as recited in claim 11 wherein at least one of said ramp and lug are made of elastically deformable material.

13. The rotary lock of claim 1 wherein a spring engages the syringe body and the sheath to normally urge the sheath to its extended position covering the needle, whereby permanently locking the latch locks the sheath in its extended protective position.

14. The rotary lock of claim 1 wherein a spring interconnects the syringe body and the reciprocal latch to normally urge the latch to a position latching the sheath in its extended position covering the needle.

15. The rotary lock of claim 1 wherein the lugs have inclined surfaces that are parallel to the ramps when the ramps and lugs are in engagement.

16. The lock of claim 11 wherein the latch is a rotatable ring disposed on the exterior of the sheath and the one of the sheath and the latch ring holding the ramp has a longitudinal slot that permits the lug to reciprocate in the slot to allow the sheath to be withdrawn from the needle.

17. In a syringe having:
   (a) a hollow syringe body having a longitudinal axis,
   (b) a hollow needle communicating with the hollow syringe body,
   (c) a sheath reciprocal along said axis to cover and uncover the needle,
   (d) a latch finger connected the sheath and elongated along said axis and having a free end that normally projects outwardly of said sheath and is movable inwardly to latch the sheath to the syringe body, and
   (e) a latch disposed on said sheath and reciprocal thereon to engage the latch finger to latch and unlatch the syringe body and sheath and movable transversely to said body axis, a lock for said latch comprising:
   1) a ramp in a plane transverse to the body axis and terminating in a recess and connected to one of said latch and sheath; and 2) a lug connected to the other of said latch and sheath and disposed adjacent to the ramp, whereby relative rotation of the latch and the sheath causes the lug to climb the ramp and drop into the recess and thereby permanently lock the latch in a position that holds the sheath covering the needle.

18. In a syringe having:
(a) a hollow syringe body having a longitudinal axis,
(b) a hollow needle communicating with the hollow syringe body,
(c) a sheath reciprocal along said axis to cover and uncover the needle, and
(d) a latch movable on said sheath to latch the sheath n its extended position over the needle or to unlatch the sheath for retracting the sheath to expose the needle, a lock for the latch comprising:
1) a ramp in a plane transverse to the body axis and terminating in a recess and connected to one of said latch and sheath; and
2) a lug connected to the other of said latch and sheath and disposed adjacent to the ramp, whereby relative rotation of the latch and the sheath causes the lug to climb the ramp and drop into the recess and thereby permanently lock the latch in a position that holds the sheath in a position covering the needle.

* * * * *